(12) United States Patent
Oh et al.

(10) Patent No.: US 12,235,230 B2
(45) Date of Patent: Feb. 25, 2025

(54) CARBON-BASED OPTICAL SENSOR ELEMENT FOR MEASURING GREENHOUSE GAS CONCENTRATION

(71) Applicant: National Institute of Meteorological Sciences, Seogwipo-si (KR)

(72) Inventors: Young Suk Oh, Seogwipo-si (KR); Su Ryon Shin, Wellesley, MA (US); Hyun Young Jung, Jinju-si (KR); Sang Won Joo, Seogwipo-si (KR); Hae Young Lee, Seogwipo-si (KR); Chang Kee Lee, Seoul (KR); Yeon Hee Kim, Seogwipo-si (KR); Chu Yong Chung, Seogwipo-si (KR)

(73) Assignee: National Institute of Meteorological Sciences, Seogwipo-si (KR)

( * ) Notice: Subject to any disclaimer, the term of this patent is extended or adjusted under 35 U.S.C. 154(b) by 496 days.

(21) Appl. No.: 17/719,623

(22) Filed: Apr. 13, 2022

(65) Prior Publication Data
US 2023/0168213 A1 Jun. 1, 2023

(51) Int. Cl.
*B82Y 15/00* (2011.01)
*G01N 23/227* (2018.01)
*G01N 33/00* (2006.01)

(52) U.S. Cl.
CPC ............ *G01N 23/227* (2013.01); *B82Y 15/00* (2013.01); *G01N 33/0036* (2013.01); *G01N 2223/084* (2013.01); *G01N 2223/638* (2013.01)

(58) Field of Classification Search
CPC .. G01N 23/227; G01N 27/12; G01N 33/0036; G01N 33/004; G01N 2233/084; G01N 2233/638; B82Y 15/00
See application file for complete search history.

(56) References Cited

U.S. PATENT DOCUMENTS

| 9,090,476 | B2 * | 7/2015 | Chang | C01B 32/184 |
| 9,746,373 | B2 * | 8/2017 | Oh | G01J 3/0232 |
| 11,692,932 | B2 * | 7/2023 | Lievois | G01M 3/38 |
| | | | | 250/339.06 |

OTHER PUBLICATIONS

Kim et al., "Ambient $CO_2$ Measurement Using Raman Lidar", Korean Journal of Remote Sensing, vol. 35, No. 6-3, 2019, pp. 1187-1195.

* cited by examiner

*Primary Examiner* — Justin N Olamit
(74) *Attorney, Agent, or Firm* — Knobbe, Martens, Olson, & Bear, LLP

(57) ABSTRACT

This application relates to an optical sensor element. In one aspect, the optical sensor element includes a graphite column including one or more graphite rods. The optical sensor element may also include one or more first graphene layers partly or entirely covering each of both ends of the graphite column. The optical sensor element may further include one or more second graphene layers partly or entirely covering the outer circumferential surface of the graphite column. This application also relates to an optical sensor for measuring the concentration of a greenhouse gas and the optical sensor includes the optical sensor element.

6 Claims, 11 Drawing Sheets

CARBON-BASED OPTICAL SENSOR ELEMENT FOR MEASURING GREENHOUSE GAS CONCENTRATION

CROSS REFERENCE TO RELATED APPLICATION

The present application claims priority to Korean Patent Application No. 10-2021-0170314, filed Dec. 1, 2021, the entire content of which is incorporated herein for all purposes by this reference.

BACKGROUND

Technical Field

The present disclosure relates to a sensing material included in an optical sensor capable of measuring the concentration of greenhouse gas or the like on the basis of the photoelectric effect.

Description of Related Technology

With the strengthened Paris Agreement that took effect in January 2021 and the adaption of carbon neutrality in the international community, efforts to fight against climate change are more strongly demanded than ever before. To scientifically support this, a dense observation network is required, and the World Meteorological Organization (WMO) places importance on the development of low-cost (LC) observation equipment and network construction by observing atmospheric composition such as greenhouse gas concentrations in urban and non-urban areas.

SUMMARY

The technical problem to be solved by the present disclosure is to provide a new greenhouse gas measurement device that can implement a greenhouse gas concentration monitoring technology, such as a device capable of accurately measuring the average greenhouse gas concentration over a wide area.

To solve the above technical problem, the present disclosure provides an optical sensor element including: a graphite column including one or more graphite rods; one or more graphene layers partly or entirely covering each end of the graphite column; and one or more graphene layers partly or entirely covering the outer circumferential surface of the graphite column.

The optical sensor element according to the present disclosure is a photon detector that generates photoelectrons having energy exceeding a work function by a photoelectric effect when natural light such as sunlight or artificial light such as LED lighting is received.

According to the present disclosure, when the graphite column of the optical sensor element includes two or more graphite rods, the optical sensor element may have a bundle structure in which the two or more graphite rods are arranged side by side in the longitudinal direction.

In addition, when the graphite column includes two or more graphite rods, the surface of each graphite rod may be coated with one or more graphene layers.

That is, as shown in FIG. 1A, the graphite rod included in the graphite column may have a structure in which the upper and lower surfaces and the entire outer circumferential surface are covered with one or more graphene layers.

FIG. 1B is a diagram schematically showing how electrons are generated and flow when light is emitted to the optical sensor element according to the present disclosure.

When the element is irradiated with light, incidence light causes excitation at a first end of the graphite column, thereby generating photoelectrons having energy exceeding a work function. These photoelectrons generate a potential difference between the first end and a second end of the graphite column, and the graphene layer(s) surrounding the first and second ends and outer circumferential surface of the graphite column function as a channel for rapid movement of the photoelectrons from the first end to the second end.

At this time, as shown in FIG. 1B, the photoelectrons are most effectively generated on the upper surface (i.e., the surface of the first end) where the graphene layer meets the graphite column, and the generated photoelectrons vertically move downward from the upper surface of the element to the lower surface. That is, the photoelectrons move along the graphite column side surfaces covered with the graphene layers.

In addition, the optical sensor element according to the present disclosure has excellent sensitivity with respect to all wavelength ranges including infrared, visible, and ultraviolet rays, and exhibits a linear relationship between a voltage and a current density. Therefore, the optical sensor element according to the present disclosure is advantageous in realizing an optical sensor-based measuring device.

A method of manufacturing the optical sensor element according to the present disclosure is not particularly limited. For example, a graphite sheet is synthesized from graphene under high temperature and pressure, and the graphite sheet is laminated in a predetermined direction such as a thickness direction, and then treated under high temperature and pressure to form a carbon column in which graphite rods are arranged side by side in a longitudinal direction thereof. Next, a graphene layer is formed to surround the outer circumferential surface of the carbon column, and both longitudinal end surfaces, i.e., upper and lower surfaces, of the carbon column are coated with graphene to manufacture an optical sensor element.

Furthermore, the present disclosure includes a proposal for a greenhouse gas concentration measuring optical sensor including the optical sensor element.

The optical sensor element according to the present disclosure has a simple structure and effectively responds to the optical characteristics of various atmospheric environments. In addition, even though the response pattern to optical signals is the same, the optical sensor element can accurately reflect the characteristics of charge accumulation-loss for optical signals according to atmospheric environmental variables such as incident angle or light intensity, duration and interval of light signal, or the like. Therefore, the optical sensor element is useful for implementation of a measurement device that can accurately and stereoscopically measure the concentration of greenhouse gases in the air on the basis of an optical sensor.

BRIEF DESCRIPTION OF THE DRAWINGS

The above and other objects, features, and other advantages of the present disclosure will be more clearly understood from the following detailed description taken in conjunction with the accompanying drawings.

DETAILED DESCRIPTION

Figure 1A:
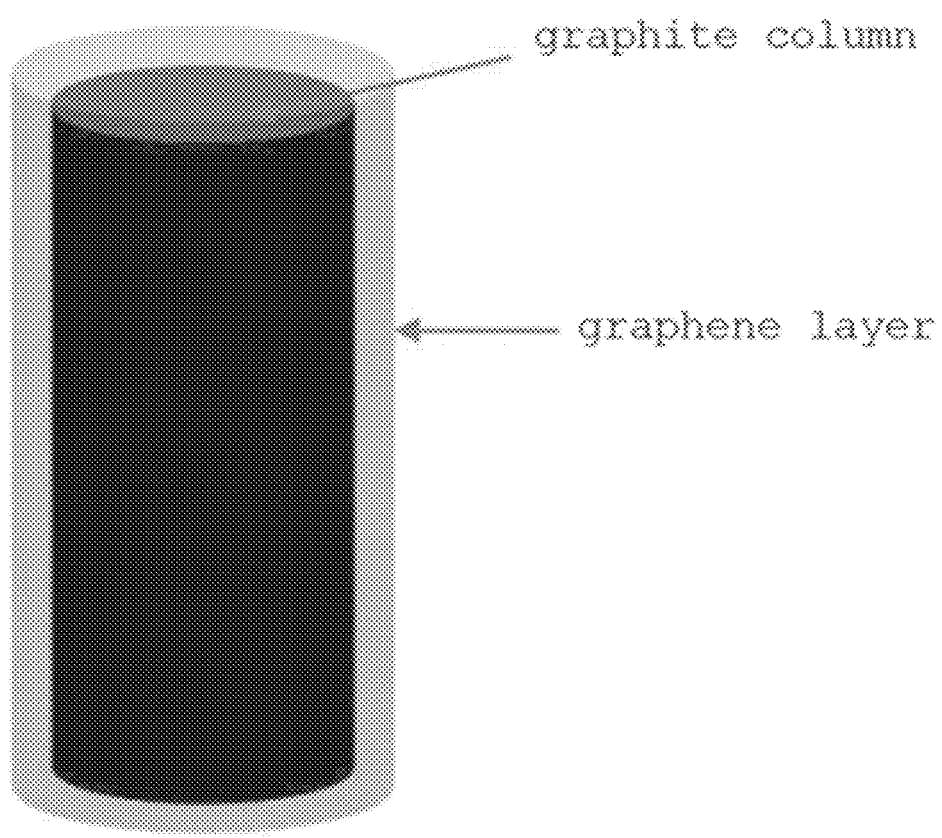
FIG. 1A is a schematic view illustrating an example of a graphite rod constituting a graphite column of an optical sensor element according to the present disclosure.
Figure 1B:
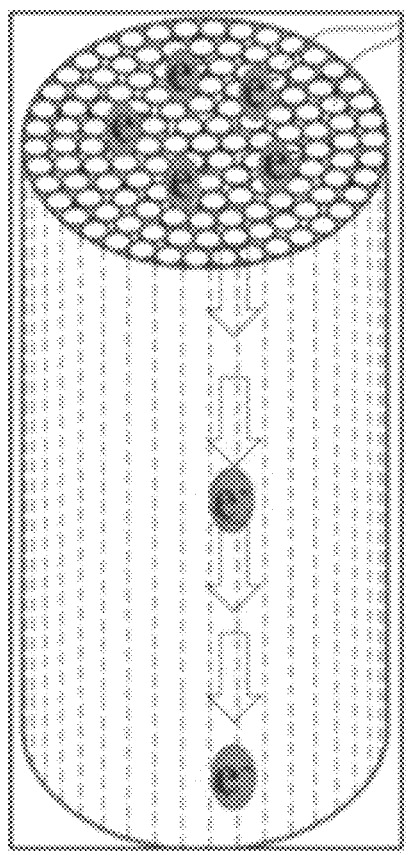
FIG. 1B is a schematic view illustrating the generation and movement of photoelectrons when the optical sensor element (including the graphite column in which the graphite rods are bundled as illustrated in FIG. 1A) according to the present disclosure.

The low accuracy of the LC observation equipment has been pointed out as a limiting point so far, and most of the existing LC observation devices for measuring greenhouse gas concentrations use the measurement technology that can be used in very limited small areas where observation sensors are in direct contact with the actual atmospheric environment. Therefore, the existing LC observation devices have a limitation in that they cannot measure the concentration of greenhouse gases over a wide area.

In describing the present disclosure, well-known functions or constructions will not be described in detail when it is determined that they may obscure the gist of the present disclosure.

Since embodiments in accordance with the concept of the present disclosure can undergo various changes and have various forms, only some specific embodiments are illustrated in the drawings and described in detail in the present specification. While specific embodiments of the present disclosure are described herein below, they are only for illustrative purposes and should not be construed as limiting to the present disclosure. Thus, the present disclosure should be construed to cover not only the specific embodiments but also cover all modifications, equivalents, and substitutions that fall within the concept and technical spirit of the present disclosure.

The terminology used herein is for the purpose of describing particular embodiments only and is not intended to be limiting. As used herein, the singular forms "a", "an", and "the" are intended to include the plural forms as well unless the context clearly indicates otherwise. It will be further understood that the terms "comprise" or "has" when used in the present specification specify the presence of stated features, regions, integers, steps, operations, elements and/or components, but do not preclude the presence or addition of one or more other features, regions, integers, steps, operations, elements, components and/or combinations thereof.

Hereinafter, the present disclosure will be described in more detail by way of examples.

Examples according to the present disclosure can be modified into various other forms, and the scope of the present disclosure is not construed as being limited to the examples described below. Examples are provided to help the ordinarily skilled in the art to more thoroughly understand the present disclosure.

Example

Figure 10:
FIG. 10 is a table showing the magnitudes of the dark current and the peak current of all the samples "1290-2 Gr(O)", "1290-2 Gr(X)", and "1290-1" in atmospheric and vacuum conditions, is an image of a test apparatus, in which the 1290-2 Gr(O) sample shows a value of 95.2 mS/cm in a vacuum condition.

C19 graphene was laminated in several layers and then exposed to heat of a temperature of about 2000° C. under 100 to 200 atm for about 2 weeks to synthesize graphite, and the graphite was processed into a cylindrical sample (See 1209-1 sample in FIG. 10).

In addition, the synthesized graphite is stacked in the direction of thickness and then exposed to a high temperature of about 1000° C. and a high pressure of 100 atm so that a specimen was prepared. The specimen had a structure in which graphite rods are arranged side by side in the longitudinal direction to form a carbon column, and the outer circumferential surface of the carbon column is covered with a grapheme layer (See 1290-2Gr(X) sample in FIG. 10).

In addition, graphene was coated on the upper and lower surfaces of the carbon column of the 1290-2Gr(X) sample. That is, a specimen in which both of the end surfaces and the outer circumferential surface of the carbon column were coated with graphene was prepared (See 1290-2Gr(O) sample in FIG. 10).

Figure 2:
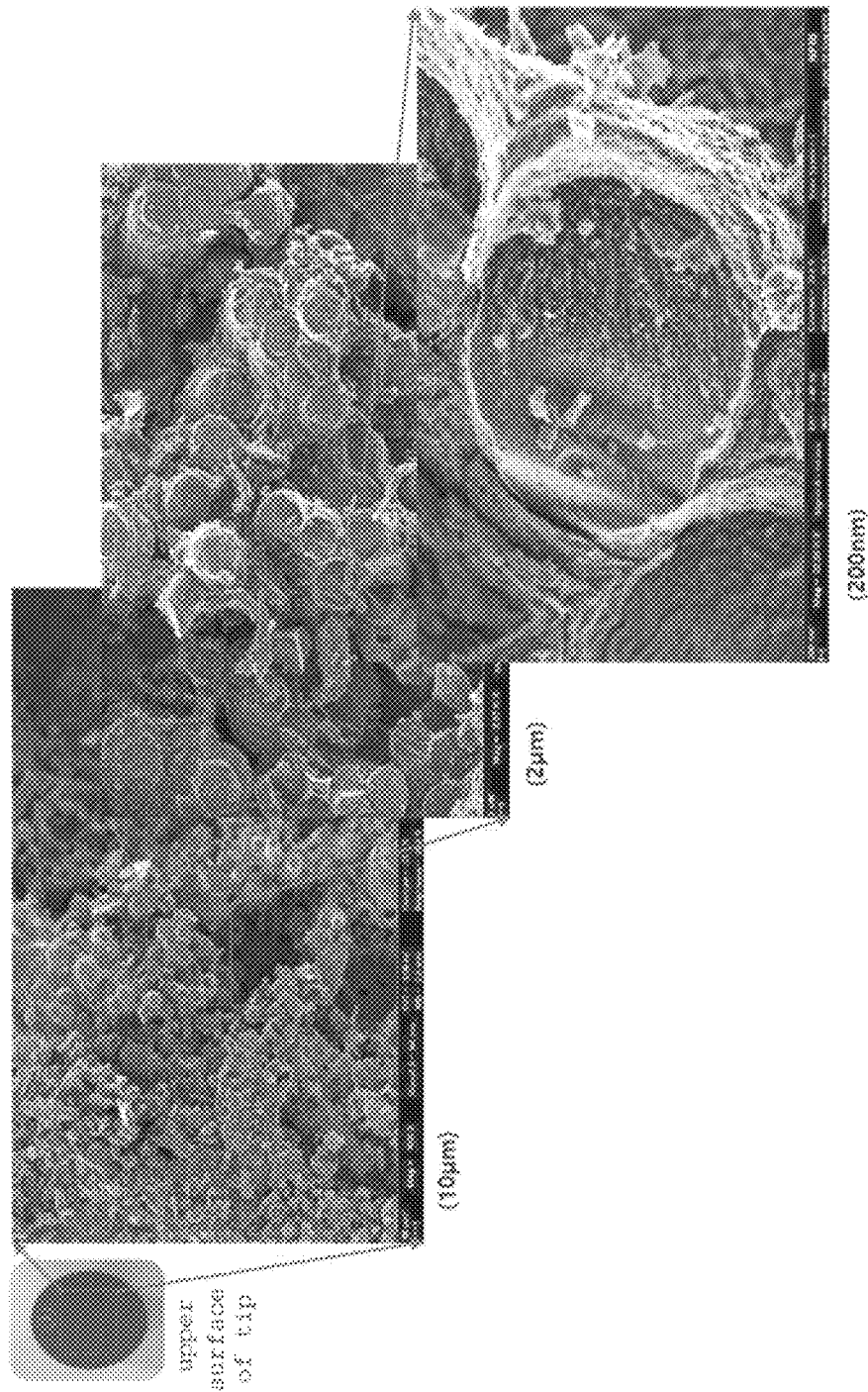
FIG. 2 is a scanning electron microscope (SEM) image of the upper surface of a 1290-2 Gr(O) sample prepared in an example of the present application.

FIG. 2 is a scanning electron microscope (SEM) image of the upper surface of the 1290-2Gr(O) sample. Referring to FIG. 2, graphene is rolled into a single layer on each graphite rod to cover the surface. It is confirmed that a single layer of grapheme is formed on the surface of the graphite column having a bundle structure in which the graphite rods are arrayed.

Figure 3:
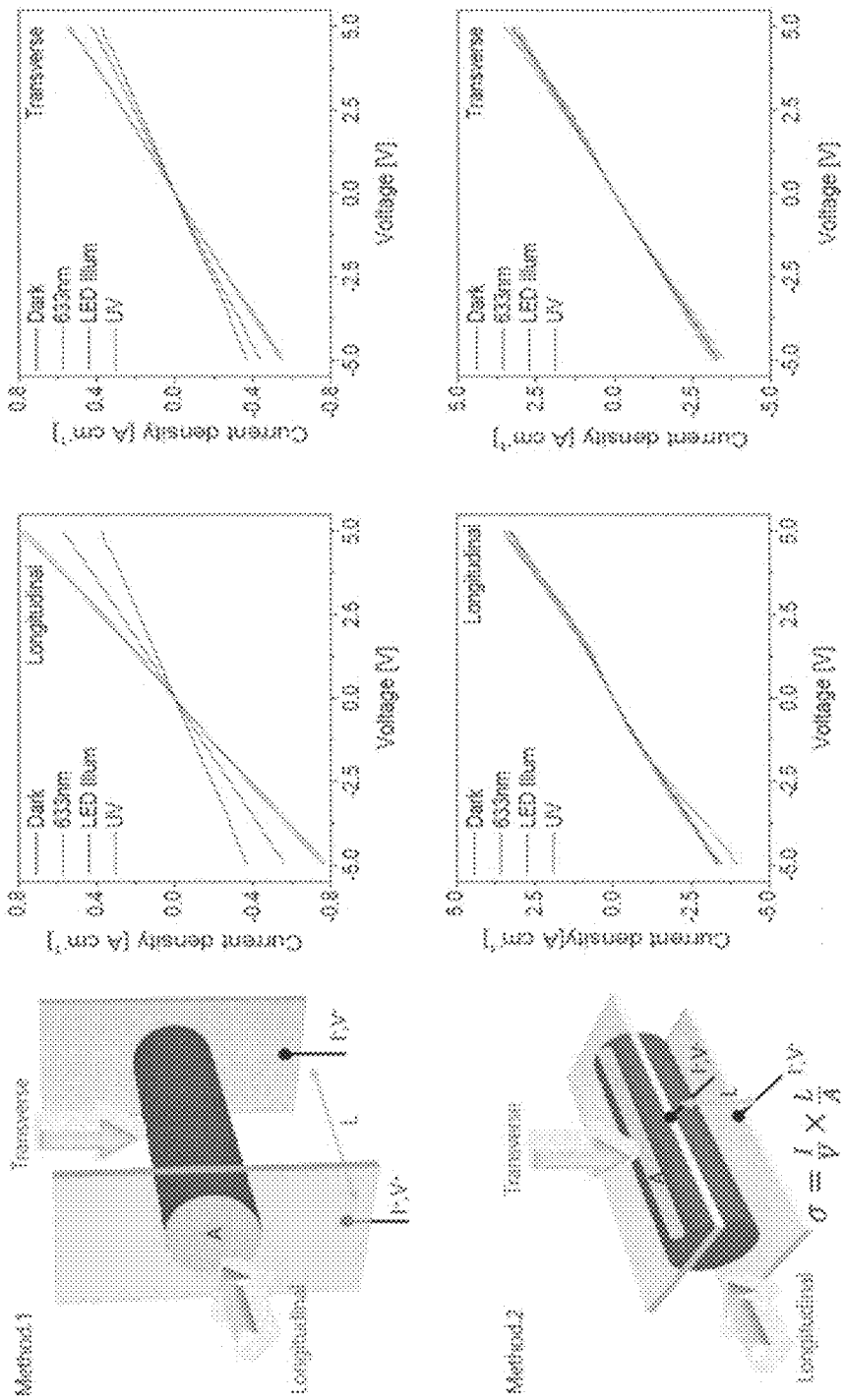
FIG. 3 is an experimental design for comparing the current density generated by photoelectrons on the upper surface of the surface and the current density generated by photoelectrons on the side surface of the 1290-2 Gr(O) sample, and also shows information about the movement direction of the generated electrons.

FIG. 3 shows photoelectrons generated by incident light and a result of comparison in the current density generated by the photoelectrons between on the upper surface and on the side surface of the 1290-2Gr(O) sample. This comparison was performed to investigate which direction of movement of the photoelectrons causes higher current density. In the structure described above, when electrons are generated on the upper surface by the light introduced from the outside, there is a potential difference between the upper and lower surfaces of the graphite column, and the photoelectrons naturally move downward from the upper surface to the lower surface where the photoelectrons are not generated. A structure in which graphene and graphite are vertically arranged moves electrons to the bottom quickly, and minimizes the loss of photoelectrons by lowering the probability of photoelectrons re-entering the electron orbit.

Figure 4:
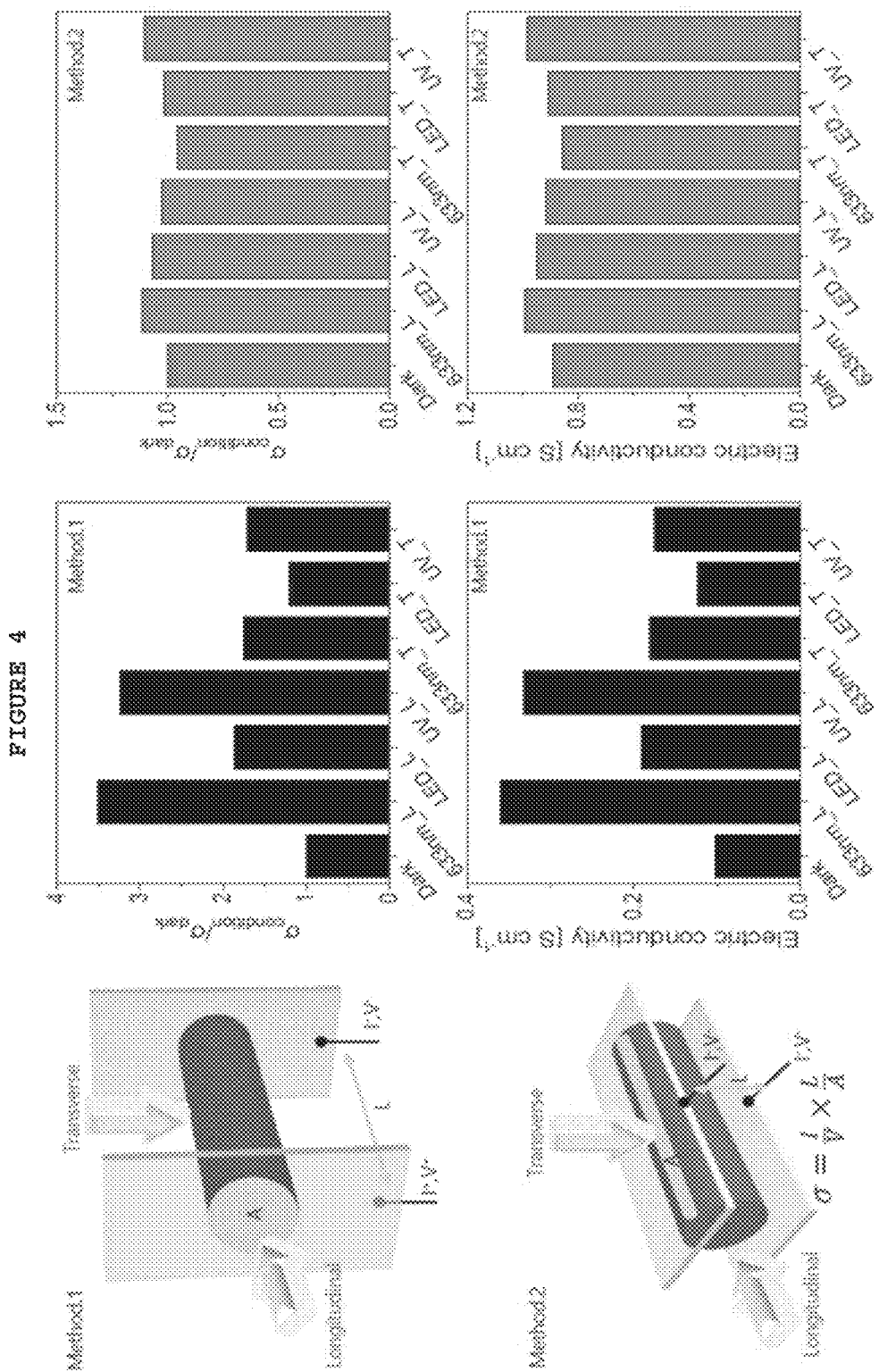
FIG. 4 shows the electrical conductivity and ratio according to the direction of light incident on the 1290-2 Gr(O) sample and the direction of electrons.

FIG. 4 shows a graphite and graphene mixed sample structure, an electric conductivity for an electron movement direction (parallel or perpendicular), and a ratio of electric conductivity to dark current when photoelectrons generated by light incident on the 1290-2Gr(O) sample move downward (i.e., move to a first area opposite to a second area where the photoelectrons are generated). When the electron movement direction is parallel to the structure of the 1290-2Gr(O) sample, changes in all of the values described above are small. In such a structure, graphite serves as a conducting wire that moves photoelectrons in a downward direction.

Figure 5:
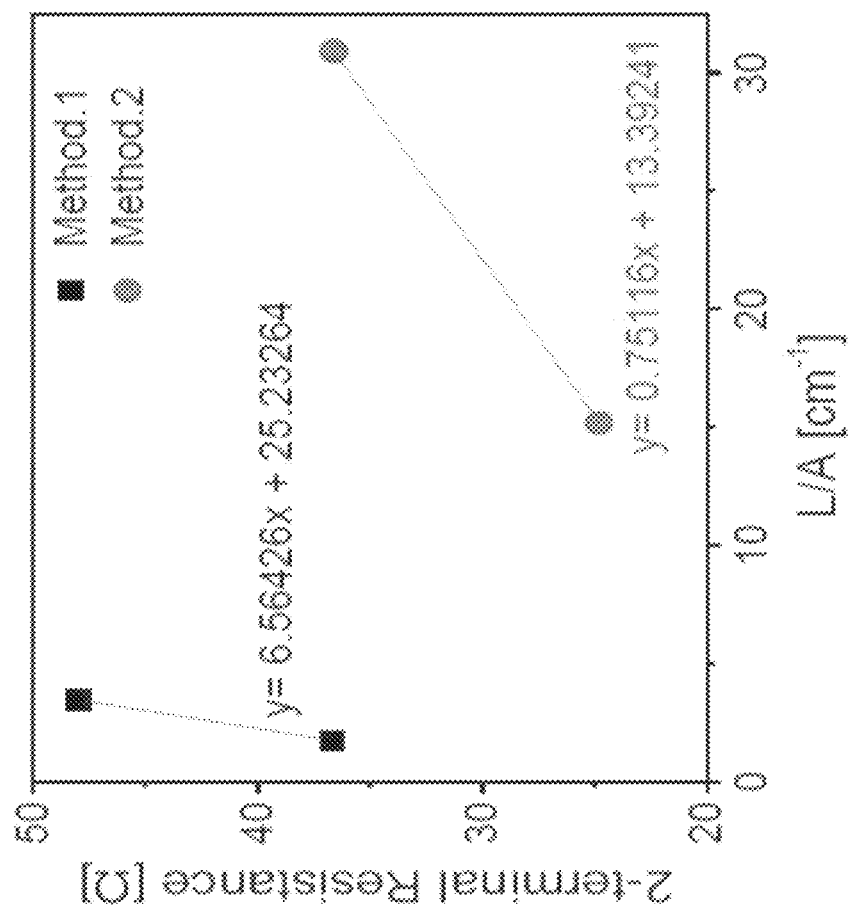
FIG. 5 shows a functional relationship between the terminal resistance and the distance/area ratio in the 1290-2 Gr(O) sample, in which the result shows that the current density appears to linearly changes according to a voltage, indicating that the optimal condition is that light is incident on the upper surface of the sample and electrons move in the vertical direction in the sample, and it is necessary to find the optimum thickness because as the movement distance of electrons increases, the resistance increases.

FIG. 5 is a graph showing the characteristics of FIGS. 3 and 4 as a function of resistance and area/distance. The 1290-2Gr(O) sample is configured such that photoelectrons are generated within the maximum and minimum ranges corresponding to the area irradiated with sunlight after the 1290-2Gr(O) sample receives light. The electrons are output as an electrical signal. That is, since information is provided one-dimensionally without intervention of other processing steps or additional devices such as an interferometer, there is no distortion of information and the processing speed is fast. In addition, a very rare characteristic that the current density linearly changes with the voltage is exhibited. For this reason, the element may find various applications such as greenhouse gas sensors and energy converters. However, the resistance of the structure acting as a conductor increases with length. Therefore, it is required that photoelectrons are generated and moved under appropriate length conditions.

Figure 6:
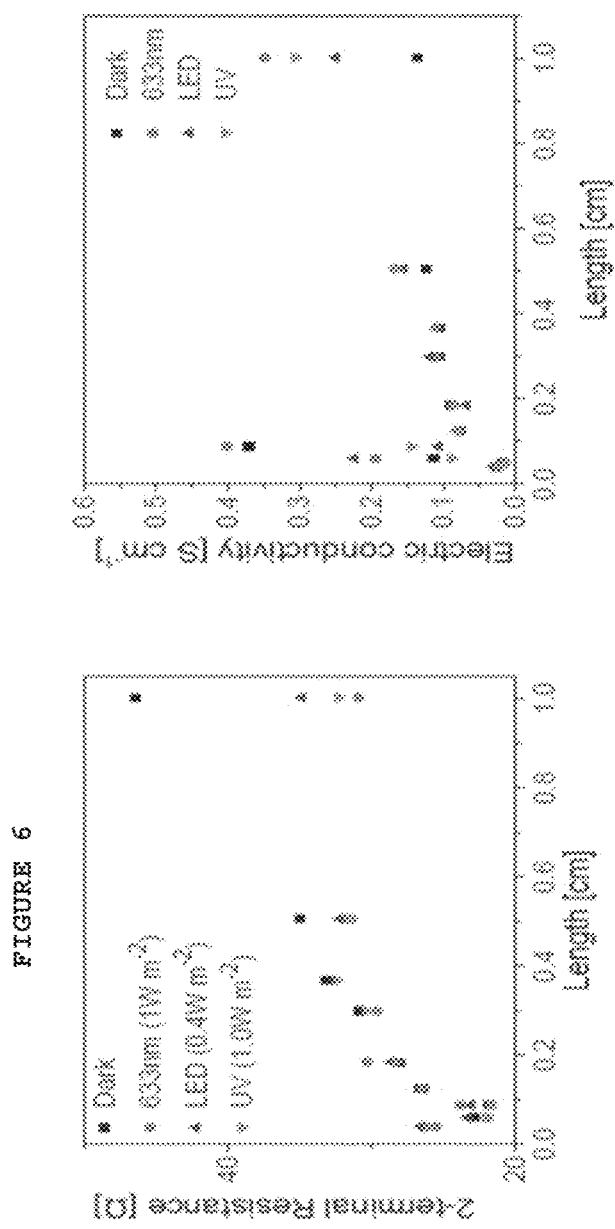
FIG. 6 shows a relationship between the length of a light incidence area and the terminal resistance of the 1290-2 Gr(O) sample, thereby indicating how the electrical conductivity appears.

Referring to FIG. 6, light of several wavelengths is incident on the upper surface of the 1290-2Gr(O) sample. Thus, energy having a certain level that is equal to or higher than a predetermined level corresponding to a work function for emitting electrons is supplied to a carbon atom electron cloud on a graphene surface, and electrons having a higher energy level than that are separated. The separated electrons are moved by graphite arranged in a vertical direction. At this time, the terminal resistance and electric conductivity according to the movement distance of the electrons were analyzed on the basis of the dark current. This provides optimal distance information (0.8 mm) of the generated photoelectrons.

Figure 7:
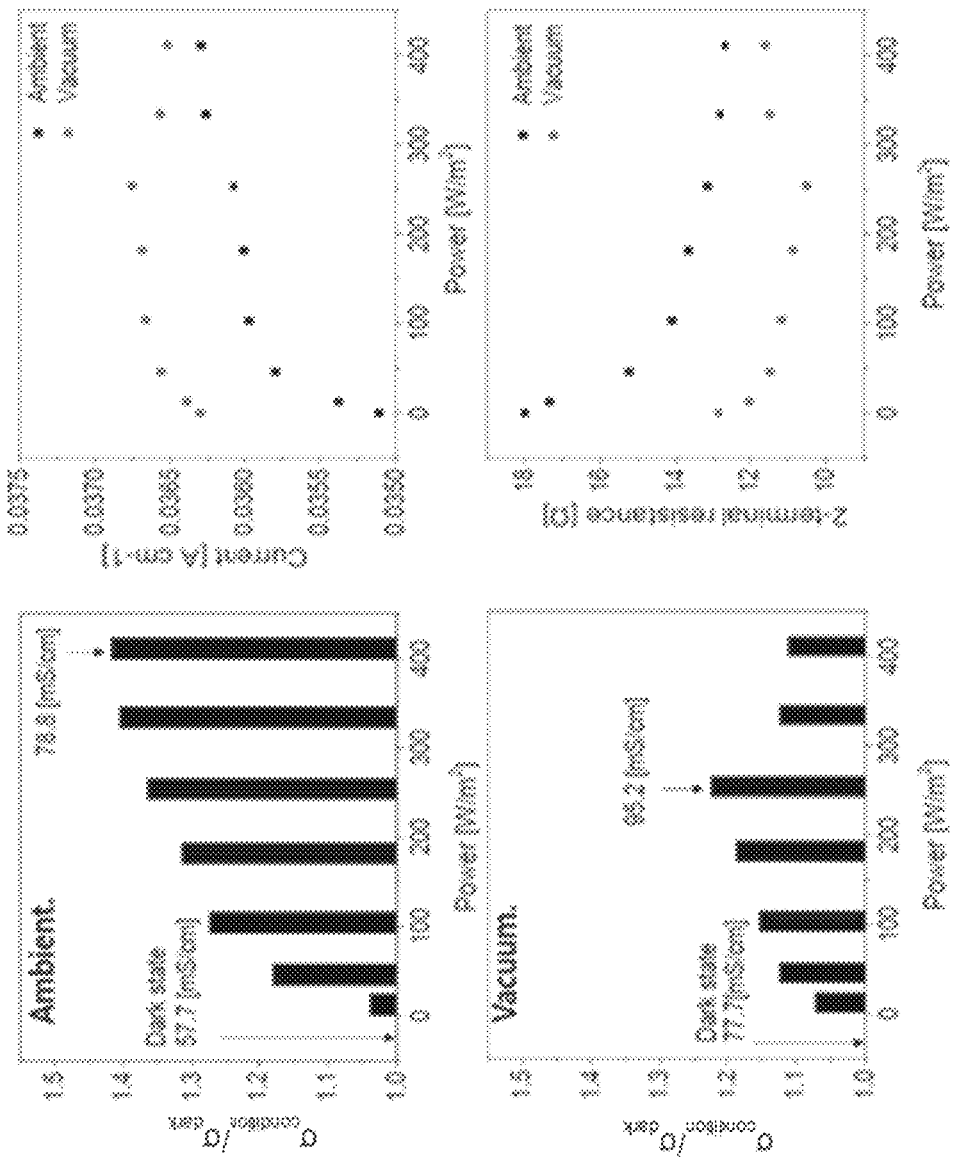
FIG. 7 is a result showing changes in current and terminal resistance in ambient and vacuum environments when the 1290-2Gr(O) sample has the optimum thickness, in which current and resistance are significantly improved.
Figure 8:
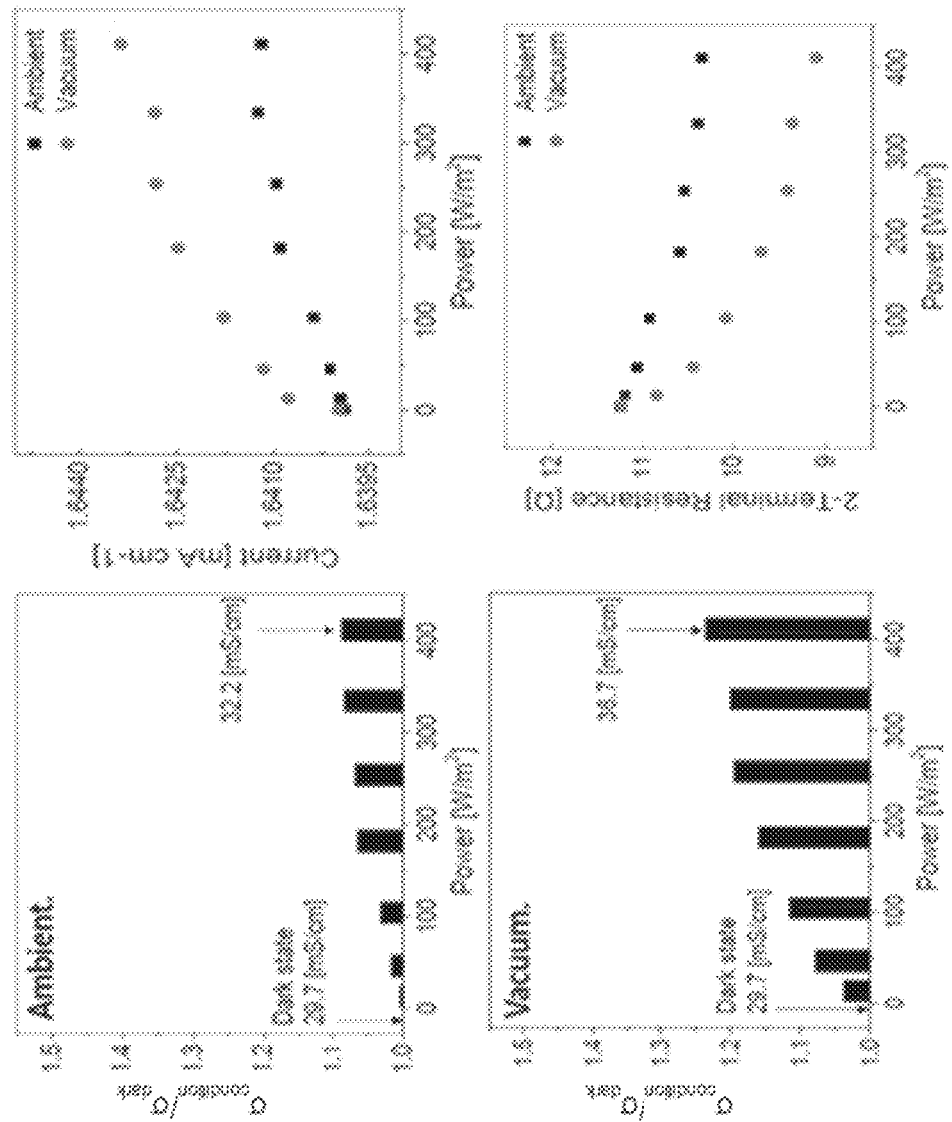
FIG. 8 is a result showing changes in current and terminal resistance in ambient and vacuum environments when a 1290-2Gr(X) sample has the optimum thickness.
Figure 9:
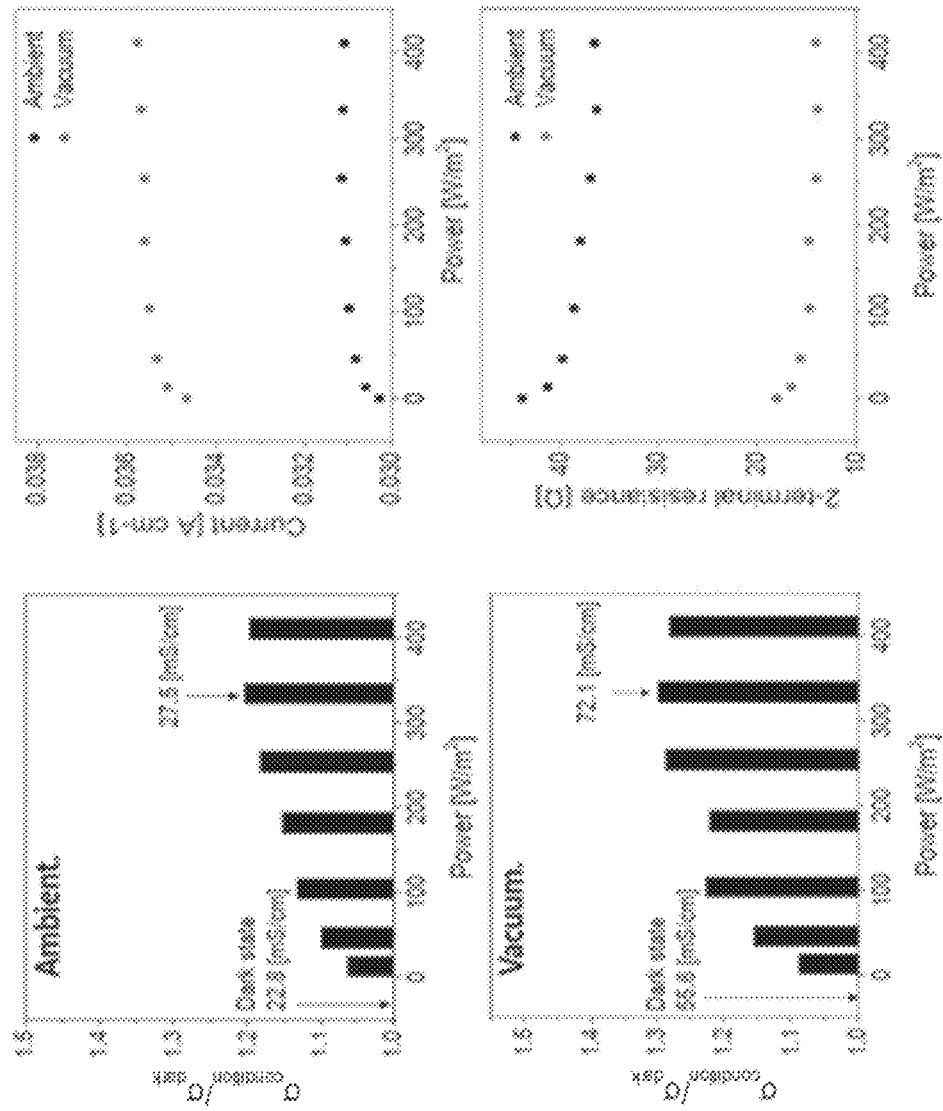
FIG. 9 is a result showing changes in current and terminal resistance in ambient and vacuum environments when a 1290-1 sample has the optimum thickness.

FIGS. 7, 8, and 9 show an analysis result in which photoelectrons generated by the intensity of light incident on the 1290-2Gr(O) sample, the 1290-2Gr(X) sample, and the 1290-1 sample are analyzed with changes in current and resistance in vacuum and atmospheric environments. The difference between the 1290-2Gr(O) and 1290-2Gr(X) samples is the presence and absence of a single graphene layer on the surface where the light source is incident, and the 1290-1 sample is a composite of graphite and graphene and has a structure different from the former two samples. Such sample configurations are designed to investigate the generation and movement of photoelectrons and the potential difference according to structures, with reference to the 1290-2Gr(O) sample. It is characterized in that graphite are stacked in the vertical direction, and the generated photoelectrons move from a first end where the photoelectrons are generated to a second end which is opposite to the first end along the graphite, and at which photoelectrons are not generated due to the potential difference between the first end and the second end of the graphite column.

FIG. 10 is a table of dark current and highest electric conductivity of the 1290-2Gr(O), 1290-2Gr(X), and 1290-1 samples, in which the values are measured under atmospheric and vacuum conditions. The table shows the values regarding the movement of the photoelectrons and the potential difference when the photoelectrons move to a region opposite to the region where they are generated. From the table, it is possible to calculate the movement speed of the generated photoelectrons, the loss of photoelectrons, and the like when the graphite serves as a conductive wire through which the photoelectrons move downward.

While exemplary embodiments of the present disclosure have been described with reference to the accompanying drawings, those skilled in the art will appreciate that the present disclosure can be implemented in other different forms without departing from the technical spirit or essential characteristics of the present disclosure. Therefore, it can be understood that the examples described above are only for illustrative purposes and are not restrictive in all aspects

What is claimed is:

1. An optical sensor element comprising:
a graphite column comprising two or more graphite rods;
one or more first graphene layers partially or entirely covering each of first and second ends of the graphite column; and
one or more second graphene layers partially or entirely covering an outer circumferential surface of the graphite column.

2. The optical sensor element of claim 1, wherein the graphite column has a bundle structure in which the two or more graphite rods are arranged side by side.

3. The optical sensor element of claim 1,
wherein a surface of each of the two or more graphite rods is covered with one or more graphene layers.

4. The optical sensor element of claim 1, wherein incidence light is configured to cause excitation to generate photoelectrons at the first end of the graphite column and wherein the photoelectrons are configured to vertically move toward the second end of the graphite column through the graphite column and along the surface of the graphite column.

5. The optical sensor element of claim 1, wherein current density is configured to linearly increase with intensity of incident light due to movement of photoelectrons.

6. An optical sensor for measuring a concentration of a greenhouse gas, the optical sensor comprising an optical sensor element, the optical sensor element comprising:
a graphite column comprising one or more graphite rods;
one or more first graphene layers partially or entirely covering each of first and second ends of the graphite column; and
one or more second graphene layers partially or entirely covering an outer circumferential surface of the graphite column.

* * * * *